(12) United States Patent
Milner et al.

(10) Patent No.: US 6,307,036 B1
(45) Date of Patent: Oct. 23, 2001

(54) TUMOUR SUPPRESSOR GENE

(75) Inventors: Jo Milner; Nik Veldhoen, both of York (GB)

(73) Assignee: Yorkshire Cancer Research, Harrogate (GB)

(*) Notice: Subject to any disclaimer, the term of this patent is extended or adjusted under 35 U.S.C. 154(b) by 0 days.

(21) Appl. No.: 09/257,580

(22) Filed: Feb. 25, 1999

(30) Foreign Application Priority Data

Feb. 28, 1998 (GB) .................................................. 9804178

(51) Int. Cl.$^7$ .......................... C07H 21/02; C12N 15/00; C12N 1/20; C12P 21/06
(52) U.S. Cl. .................. 536/23.1; 435/320.1; 435/253.3; 435/69.1
(58) Field of Search ........................ 536/23.1; 435/320.1, 435/252.3, 69.1

(56) References Cited

PUBLICATIONS

Leeuwen et al (Anticancer Res., 16:3737–3744), 1996.*
Kraegel et al (Cancer Lett., 92:181–186), 1996.*
Veldhoen et al.; Mutations of the p53 Gene in Canine Lymphoma and Evidence for Germ Line p53 Mutations in the Dog, *Oncogene*, 16:249–255 (1998).
Veldhoen et al.; Isolation of Canine p53 cDNA and Detailed Characterization of the Full Length Canine p53 Protein, *Oncogene*, 16:1077–1084 (1998).

* cited by examiner

*Primary Examiner*—Susan Ungar
(74) *Attorney, Agent, or Firm*—Myers Bigel Sibley & Sajovec

(57) ABSTRACT

Isolated DNA coding for canine p53 protein is described, along with vectors and host cells containing such isolated DNA. Methods for producing canine p53 protein by culturing host cells that contain such DNA are also described.

7 Claims, 15 Drawing Sheets cp53 5'up (33MER, SEVEN DEGENERATE POSITIONS)
ANNEALS TO THE CODING STRAND OF p53 cDNA

5'-GCGGTACCGGKGRCTGCMATGGARGAGAGYCRCMG-3' cp53 3'dn (33MER, SIX DEGENERATE POSITIONS)
ANNEALS TO THE NON-CODING STRAND OF p53 cDNA

5'-GCGGGATCCRAGRAYRTCAGTCTGAGTCRRGCCC-3'

NOTE: K=T+G, R=A+G, M=A+C, Y=C+T

FIG. 1

```
  -16                                              GGTACC GGTGACTGCA
    1 ATGGAGGAGT CGCAGTCAGA GCTCAATATC GACCCCCCTC TGAGCCAGGA
   51 GACATTTTCA GAATTGTGGA ACCTGCTTCC TGAAAACAAT GTTCTGTCTT
  101 CGGAGCTGTG CCCAGCAGTG GATGAGCTGC TGCTCCCAGA GAGCGTCGTG
  151 AACTGGCTAG ACGAAGACTC AGATGATGCT CCCAGGATGC CAGCCACTTC
  201 TGCCCCCACA GCCCCTGGAC CGGCCCCCTC GTGGCCCCTA TCATCCTCTG
  251 TCCCTTCCCC GAAGACCTAC CCTGGCACCT ATGGGTTCCG TTTGGGGTTC
  301 CTGCATTCCG GGACAGCCAA GTCTGTTACT TGGACGTACT CCCCTCTCCT
  351 CAACAAGTTG TTTTGCCAGC TGGCGAAGAC CTGCCCCGTG CAGCTGTGGG
  401 TCAGCTCCCC ACCCCACCC AATACCTGCG TCCGCGCTAT GGCCATCTAT
  451 AAGAAGTCGG AGTTCGTGAC CGAGGTTGTG CGGCGCTGCC CCACCATGA
  501 ACGCTGCTCT GACAGTAGTG ACGGTCTTGC CCTCCTCAG CATCTCATCC
  551 GAGTGGAAGG AAATTTGCGG GCCAAGTACC TGGACGACAG AAACACTTTT
  601 CGACACAGTG TGGTGGTGCC TTATGAGCCA CCCGAGGTTG GCTCTGACTA
  651 TACCACCATC CACTACAACT ACATGTGTAA CAGTTCCTGC ATGGGAGGCA
  701 TGAACCGGCG GCCCATCCTC ACTATCATCA CCCTGGAAGA CTCCAGTGGA
  751 AACGTGCTGG GACGCAACAG CTTTGAGGTA CGCGTTTGTG CCTGTCCCGG
  801 GAGAGACCGC CGGACTGAGG AGGAGAATTT CCACAAGAAG GGGGAGCCTT
  851 GTCCTGAGCC ACCCCCGGG AGTACCAAGC GAGCACTGCC TCCCAGCACC
  901 AGCTCCTCTC CCCCGCAAAA GAAGAAGCCA CTAGATGGAG AATATTTCAC
  951 CCTTCAGATC CGTGGGCGTG AACGCTATGA GATGTTCAGG AATCTGAATG
 1001 AAGCCTTGGA GCTGAAGGAT GCCCAGAGTG GAAAGGAGCC AGGGGGAAGC
 1051 AGGGCTCACT CCAGCCACCT GAAGGCAAAG AAGGGGCAAT CTACCTCTCG
 1101 CCATAAAAAA CTGATGTTCA AGAGAGAAGG GCTTGACTCA GACTGAGGTT
 1151 AAGGATCC
```

FIG. 2

```
   1  AUGGAGGAGU CGCAGUCAGA GCUCAAUAUC GACCCCCCUC UGAGCCAGGA
  51  GACAUUUUCA GAAUUGUGGA ACCUGCUUCC UGAAAACAAU GUUCUGUCUU
 101  CGGAGCUGUG CCCAGCAGUG GAUGAGCUGC UGCUCCCAGA GAGCGUCGUG
 151  AACUGGCUAG ACGAAGACUC AGAUGAUGCU CCCAGGAUGC CAGCCACUUC
 201  UGCCCCCACA GCCCCUGGAC CGGCCCCCUC GUGGCCCCUA UCAUCCUCUG
 251  UCCCUUCCCC GAAGACCUAC CUGGCACCU AUGGGUUCCG UUUGGGGUUC
 301  CUGCAUUCCG GACAGCCAA GUCUGUUACU GGACGUACU CCCCUCUCCU
 351  CAACAAGUUG UUUUGCCAGC UGGCGAAGAC CUGCCCCGUG CAGCUGUGGG
 401  UCAGCUCCCC ACCCCACCC AAUACCUGCG UCCGCGCUAU GGCCAUCUAU
 451  AAGAAGUCGG AGUUCGUGAC CGAGGUUGUG CGGCGCUGCC CCACCAUGA
 501  ACGCUGCUCU GACAGUAGUG ACGGUCUUGC CCCUCCUCAG CAUCUCAUCC
 551  GAGUGGAAGG AAAUUUGCGG GCCAAGUACC UGGACGACAG AAACACUUUU
 601  CGACACAGUG UGGUGGUGCC UUAUGAGCCA CCCGAGGUUG GCUCUGACUA
 651  UACCACCAUC CACUACAACU ACAUGUGUAA CAGUUCCUGC AUGGGAGGCA
 701  UGAACCGGCG GCCCAUCCUC ACUAUCAUCA CCCUGGAAGA CUCCAGUGGA
 751  AACGUGCUGG GACGCAACAG CUUUGAGGUA CGCGUUUGUG CCUGUCCCGG
 801  GAGAGACCGC CGGACUGAGG AGGAGAAUUU CCACAAGAAG GGGGAGCCUU
 851  GUCCUGAGCC ACCCCCGGG AGUACCAAGC GAGCACUGCC UCCCAGCACC
 901  AGCUCCUCUC CCCGCAAAA GAAGAAGCCA CUAGAUGGAG AAUAUUUCAC
 951  CCUUCAGAUC CGUGGGCGUG AACGCUAUGA GAUGUUCAGG AAUCUGAAUG
1001  AAGCCUUGGA GCUGAAGGAU GCCCAGAGUG AAAGGAGCC AGGGGGAAGC
1051  AGGGCUCACU CCAGCCACCU GAAGGCAAAG AAGGGGCAAU CUACCUCUCG
1101  CCAUAAAAAA CUGAUGUUCA AGAGAGAAGG GCUUGACUCA GACUGA
```

FIG. 3

```
ATG GAG GAG TCG CAG TCA GAG CTC AAT ATC GAC CCC CCT CTG AGC CAG    48
MET GLU GLU SER GLN SER GLU LEU ASN ILE ASP PRO PRO LEU SER GLN
 1               5                  10                  15

GAG ACA TTT TCA GAA TTG TGG AAC CTG CTT CCT GAA AAC AAT GTT CTG    96
GLU THR PHE SER GLU LEU TRP ASN LEU LEU PRO GLU ASN ASN VAL LEU
                20                  25                  30

TCT TCG GAG CTG TGC CCA GCA GTG GAT GAG CTG CTG CTC CCA GAG AGC   144
SER SER GLU LEU CYS PRO ALA VAL ASP GLU LEU LEU LEU PRO GLU SER
            35                  40                  45

GTC GTG AAC TGG CTA GAC GAA GAC TCA GAT GAT GCT CCC AGG ATG CCA   192
VAL VAL ASN TRP LEU ASP GLU ASP SER ASP ASP ALA PRO ARG MET PRO
        50                  55                  60

GCC ACT TCT GCC CCC ACA GCC CCT GGA CCG GCC CCC TCG TGG CCC CTA   240
ALA THR SER ALA PRO THR ALA PRO GLY PRO ALA PRO SER TRP PRO LEU
 65                  70                  75                  80

TCA TCC TCT GTC CCT TCC CCG AAG ACC TAC CCT GGC ACC TAT GGG TTC   288
SER SER SER VAL PRO SER PRO LYS THR TYR PRO GLY THR TYR GLY PHE
                85                  90                  95

CGT TTG GGG TTC CTG CAT TCC GGG ACA GCC AAG TCT GTT ACT TGG ACG   336
ARG LEU GLY PHE LEU HIS SER GLY THR ALA LYS SER VAL THR TRP THR
            100                 105                 110

TAC TCC CCT CTC CTC AAC AAG TTG TTT TGC CAG CTG GCG AAG ACC TGC   384
TYR SER PRO LEU LEU ASN LYS LEU PHE CYS GLN LEU ALA LYS THR CYS
        115                 120                 125

CCC GTG CAG CTG TGG GTC AGC TCC CCA CCC CCA CCC AAT ACC TGC GTC   432
PRO VAL GLN LEU TRP VAL SER SER PRO PRO PRO PRO ASN THR CYS VAL
    130                 135                 140

CGC GCT ATG GCC ATC TAT AAG AAG TCG GAG TTC GTG ACC GAG GTT GTG   480
ARG ALA MET ALA ILE TYR LYS LYS SER GLU PHE VAL THR GLU VAL VAL
145                 150                 155                 160

CGG CGC TGC CCC CAC CAT GAA CGC TGC TCT GAC AGT AGT GAC GGT CTT   528
ARG ARG CYS PRO HIS HIS GLU ARG CYS SER ASP SER SER ASP GLY LEU
                165                 170                 175

GCC CCT CCT CAG CAT CTC ATC CGA GTG GAA GGA AAT TTG CGG GCC AAG   576
ALA PRO PRO GLN HIS LEU ILE ARG VAL GLU GLY ASN LEU ARG ALA LYS
            180                 185                 190
```

FIG. 4A

```
TAC CTG GAC GAC AGA AAC ACT TTT CGA CAC AGT GTG GTG GTG CCT TAT   624
TYR LEU ASP ASP ARG ASN THR PHE ARG HIS SER VAL VAL VAL PRO TYR
        195                 200                 205

GAG CCA CCC GAG GTT GGC TCT GAC TAT ACC ACC ATC CAC TAC AAC TAC   672
GLU PRO PRO GLU VAL GLY SER ASP TYR THR THR ILE HIS TYR ASN TYR
        210                 215                 220

ATG TGT AAC AGT TCC TGC ATG GGA GGC ATG AAC CGG CGG CCC ATC CTC   720
MET CYS ASN SER SER CYS MET GLY GLY MET ASN ARG ARG PRO ILE LEU
225                 230                 235                 240

ACT ATC ATC ACC CTG GAA GAC TCC AGT GGA AAC GTG CTG GGA CGC AAC   768
THR ILE ILE THR LEU GLU ASP SER SER GLY ASN VAL LEU GLY ARG ASN
                245                 250                 255

AGC TTT GAG GTA CGC GTT TGT GCC TGT CCC GGG AGA GAC CGC CGG ACT   816
SER PHE GLU VAL ARG VAL CYS ALA CYS PRO GLY ARG ASP ARG ARG THR
        260                 265                 270

GAG GAG GAG AAT TTC CAC AAG AAG GGG GAG CCT TGT CCT GAG CCA CCC   864
GLU GLU GLU ASN PHE HIS LYS LYS GLY GLU PRO CYS PRO GLU PRO PRO
        275                 280                 285

CCC GGG AGT ACC AAG CGA GCA CTG CCT CCC AGC ACC AGC TCC TCT CCC   912
PRO GLY SER THR LYS ARG ALA LEU PRO PRO SER THR SER SER SER PRO
        290                 295                 300

CCG CAA AAG AAG AAG CCA CTA GAT GGA GAA TAT TTC ACC CTT CAG ATC   960
PRO GLN LYS LYS LYS PRO LEU ASP GLY GLU TYR PHE THR LEU GLN ILE
305                 310                 315                 320

CGT GGG CGT GAA CGC TAT GAG ATG TTC AGG AAT CTG AAT GAA GCC TTG  1008
ARG GLY ARG GLU ARG TYR GLU MET PHE ARG ASN LEU ASN GLU ALA LEU
            325                 330                 335

GAG CTG AAG GAT GCC CAG AGT GGA AAG GAG CCA GGG GGA AGC AGG GCT  1056
GLU LEU LYS ASP ALA GLN SER GLY LYS GLU PRO GLY GLY SER ARG ALA
            340                 345                 350

CAC TCC AGC CAC CTG AAG GCA AAG AAG GGG CAA TCT ACC TCT CGC CAT  1104
HIS SER SER HIS LEU LYS ALA LYS LYS GLY GLN SER THR SER ARG HIS
            355                 360                 365

AAA AAA CTG ATG TTC AAG AGA GAA GGG CTT GAC TCA GAC TGA          1146
LYS LYS LEU MET PHE LYS ARG GLU GLY LEU ASP SER ASP OPA
            370                 375                 380
```

FIG. 4B

| PATIENT | SEX | AGE (YEARS) | BREED | TUMOUR STAGE | GENOTYPE | THERAPY | P-GLYCOPROTEIN PRE/POST TREATMENT | TIME TO RELAPSE (WEEKS) |
|---|---|---|---|---|---|---|---|---|
| 1 | FN | 7 | BULL MASTIFF | IIIA | B-CELL | COP | -/- | 35 |
| 2 | M | 4 | CROSS BREED | IIIA | B-CELL | EP | -/- | 54 |
| 3 | M | 5 | COLLIE CROSS | IIIA | B-CELL | EP | -/- | 50 |
| 4 | F | 4 | BOXER | IIIB | T-CELL | EP | -/- | 14 |
| 5 | F | 5 | GERMAN SHEPHARD | IIIA | T-CELL | EP | -/- | 7 |
| 6 | FN | 5 | BULL MASTIFF | IIIA | B-CELL | EP | -/- | 23 |
| 7 | F | 5 | IRISH SETTER | IIIA | B-CELL | EP | +/+ | NR |
| 8 | M | 3 | BULL MASTIFF | IIIA | B-CELL | COP | -/+ | NR |

SEX: M = MALE, F = FEMALE, FN = NEUTERED FEMALE.
TUMOUR STAGE AND CHEMOTHERAPY PROTOCOLS ARE DESCRIBED IN THE MATERIALS AND METHODS SECTION.
EP = EPIRIBICIN, PREDNISOLONE. COP = CYCLOPHOSPHAMIDE, VINCRISTINE, PREDNISOLONE.
NR = NO RESPONSE TO TREATMENT.

FIG. 6

| PATIENT NUMBER | AGE (YEARS) | BREED | INTACT (I)/ NEUTERED (N) | HISTOPATHOLOGY | PROGNOSIS |
|---|---|---|---|---|---|
| 1 | 10 | COLLIE CROSS | I | CARCINOMA | GUARDED |
| 2 | 12 | SPANIEL | I | CARCINOMA | GUARDED |
| 3 | 8 | LURCHER | I | CARCINOMA | GUARDED |
| 4 | 10.5 | BORDER COLLIE | I | CARCINOMA | GUARDED |
| 5[a] | 10 | LABRADOR | I | CARCINOMA | GUARDED |
| | | | | ADENOMA | GUARDED |
| 6[b] | - | - | - | - | - |
| 7 | 9 | COLLIE CROSS | N | ADENOMA | GOOD |
| 8 | 11 | OLD ENGLISH SHEEPDOG | I | ADENOMA | GOOD |
| 9 | 5 | BOXER | N | ADENOMA | GOOD |
| 10 | 17 | JACK RUSSELL TERRIER | I | SARCOMA | GUARDED |

[a] NOTE: PATIENT NUMBER 5 PRESENTED WITH TWO DISCRETE MAMMARY TUMOURS.
[b] NO CLINICAL INFORMATION WAS AVAILABLE FOR THIS PATIENT.

FIG. 8

EXON 2

GAGCTCAATATCGACCCCCTCTGAGCCAGGAGACATTTTCAGAATT

GTGGAACCTGTAAGTGGAGGGCAGGCCAGGCTCCCCACCAGCCCTCT

GGGACCCCTGCTTCTCTCTTCTCACCTGGGTAGTGGAAACGTGCTGG

GACGCAACAGCTTTGAGGTACGCGTTTGTGCCTGTCCCGGGAGAGAC

EXON 8

CGCCGGACTGAGGAGGAGAATTTCCACAAGAAGGGGGAGCCTCGTAC

CTGAGCCACCCCCGGGAGTACCAAGCGAGGTAAGCAAGCAAGACAA

GAGGAGGTGAAGGAGGGACACCTGGGTGGCTCAGGGGTTGAGCATCA

GGCATGATCCCAGGGTCCTGGGATCGAGTCCCGTGTCAGGGTCCCTG

TAGGGAGCCTGCCTCTCCCTCTGCCTATTTTTTGCCTTTGTGTGTA

TGTCTCATGAATAAATAAATATAATCTTGAAAAAAAAAAAAAAGAG

GAGGATGTGGGGCAGATACAGAGGGTGCAATTCTGCTCAAAACATAC

TCTTCTCTTGTCTTTTCCTCCTCTCTTTCCCAGCACTGCCTCCCAGC

EXON 9

ACCAGCTCCTCTCCCCGCAAAGAAGAAGCCACTAGATGGAGAATA

TTTCACCCTTCAG

FIG. 11A

TUMOUR SUPPRESSOR GENE

BACKGROUND TO THE INVENTION

Mutations of the p53 tumour suppressor gone have been observed in a number of different tumour types isolated from human cancer patients. The central role of the p53 protein in protecting cells against genotoxic damage and the high prevalence (>50%) of p53 mutations in cancer identifies this protein as an important target in the clinical diagnosis of cancer as well as in the development of more effective anticancer treatments.

Recently, mutations have been observed in partial p53 gene sequences isolated from canine cancer patients. The identification of tumour-associated canine p53 mutations indicates that the p53 protein may play an equally important role in the suppression of cancer in the dog. Characterisation of the canine p53 protein may lad to the generation of clinically relevant diagnostic reagents useful in the classification and treatment of p53-associated cancers.

Certain canine breeds display an increased disposition to cancer. In addition, there is evidence for familial-associated canine cancers. The recent identification of a p53 germ line mutation in the dog strongly suggests that inherited p53 mutations may predispose certain canine families to cancer. The identification of these canine families would be beneficial in screening for healthy individuals suitable for vital functions in the community (eg guide dogs for the blind, dogs in law enforcement). The development of a genetic screen for individual carriers of germ line p53 mutations would benefit from information on the canine p53 cDNA and full length protein. The current information describes for the first time the isolation of the complete canine p53 cDNA sequence and expression of the full length canine p53 protein. Additionally the specification describes a method of screening for healthy individuals.

STATEMENTS OF INVENTION

The present invention provides full length canine p53 protein, cDNA and RNA sequences, degenerate primers and immunological reagents based on the full length protein.

Among the uses of the present invention are the following:

1. Degenerate primers (SEQ ID NO:5; SEQ ID NO:6) have the potential to be used in the isolation of a number of different p53 cDNA from higher vertebrate organisms.

2. Canine p53 cDNA (SEQ ID NO:1) sequence can be used;

in the isolation of the complete canine p53 gene sequence to generate probes for cytogenetic screening of canine turnouts to identify tumour-associated mutations of the canine p53 gene to identify individual carriers of germ line p53 gene mutations and determine breed disposition to p53-dependent cancers to generate tumour-identified mutants for study to study p53-dependent activities in canine normal and tumour cells to express p53 protein within in vitro expression systems (eg rabbit reticulocyte lysate)

to express p53 protein in prokaryotic and eukaryotic (eg baculovirus-mediated) in vivo expression systems to determine the efficacy of anti-cancer therapies based on p53 genetic status 3. Canine p53 RNA sequence (SEQ ID NO:4) information can be used to generate probes to assess changes in the stability or expression of p53 in different cell types. Antisense probes can also be designed to interfere with canine p53 RNA expression in vivo.

4. Canine p53 protein can be used as an antigen to generate monoclonal antibodies tat are directed to both conformation-specific epitopes and primary epitopes. Such antibodies would be useful in the clinical identification of canine cancers and in the analysis of p53 protein status. Canine p53-specific antibodies may also be useful in the analysis of a canine immune response to cancer. A diagnostic assay to detect circulating antibodies in canine cancer patients that are directed towards the canine p53 protein could be developed.

In accordance with the above, the present invention provides an isolated DNA coding for the canine p53 protein. Preferably the protein has the amino acid sequence (SEQ ID NO:2) as set forth in FIG. 4 of the accompanying drawings, or is a modified form of said protein which is fictionally equivalent or associated with a predisposition to a cancer.

The present invention also provides an isolated DNA which comprises the nucleotide sequence as set forth in FIG. 2 (SEQ ID NO:1) of the accompanying drawings or a corresponding RNA. Further, the present invention provides an isolated DNA which comprises an allelic variant of the nucleotide sequence set forth in FIG. 2 (SEQ ID NO:1) of the accompanying drawings or a corresponding RNA. Additionally The present invention provides an isolated nucleic acid which is a DNA comprising a mutated form of the nucleotide sequence set forth in FIG. 2 (SEQ ID NO:1) of the accompanying drawings and associated with a predisposition to a cancer. The mutation may be an insertion or deletion mutation, a nonsense mutation or a missense mutation.

In addition the present invention provides the following:

A. Oligonucleotide primers having nucleotide sequences (SEQ ID NO:6) as set forth in FIG. 1 of the accompanying drawings, B. A replicative cloning vector which comprises an isolated DNA of the invention and a replicon operative in a host cell for said vector C. An expression vector which comprises an isolated DNA of the invention wherein the coding sequence for the canine p53 protein or modified form thereof is operably-linked to a promoter sequence capable of directing expression of said coding sequence in host cells for said vector.

D. Host cells transformed with a vector of the invention.

E. A method of producing a canine p53 protein or modified form thereof which comprises culturing host cells of the invention under conditions suitable for production of said protein and recovering said protein.

F. A method of producing a canine p53 proteus or modified from thereof in a cell-free system under conditions suitable for production of a protein which is characterised by the radiograph shown in FIG. 5 of the accompanying drawings.

G. A preparation of canine p53 protein substantially free of other canine proteins and having the amino acid sequence (SEQ ID NO:2) set forth in FIG. 4 of the accompanying drawing.

H. A reparation of a protein substantially free of other proteins, said protein being a mutated canine p53 protein obtainable by expression of a mutated form of the nucleotide sequence (SEQ ID NO:1) set forth in FIG. 2 of the accompanying drawings.

I. An antibody capable of specifically binding to a protein of the invention.

J. An antibody of the invention which is a monoclonal antibody.

K. A preparation of a polypeptide substantially free of other proteins, said polypeptide being an antigenic fragment of a protein of the invention and which is suitable for use as an immunogen to obtain an antibody of the invention.

L. A kit for detecting mutations in the canine p53 gene resulting in cancer comprising at least one oligonucleotide primer specific for the canine p53 gene and instructions relating to detecting mutations in the canine p53 gene.

M. A kit for detecting mutations in the canine p53 gene resulting in susceptibility to cancer comprising at least one allele-specific oligonucleotide probe for the p53 gene and instructions relating to detecting mutations in the canine p53 gene.

N. A kit for detecting circulating antibodies linked with development of canine cancer involving wild type or mutant p53 and instructions relating to detecting p53 protein.

O. A kit for immunocytochemical detection of p53 abnormalities associated with canine cancer and instructions relating to the detection of p53 protein.

The invention also provides a method of identifying individual carriers of germ line p53 gene mutations, the method comprising the steps of obtaining a sample from the individual to be screened, isolating generic DNA from said sample preferably by using a reverse transcriptase polymerase chain reaction (RT-PCR), sequencing the sample and comparing it to the nucleotide sequence (SEQ ID NO:1) as set forth in FIG. 2 of the accompanying drawing, or a modified form thereof which is functionally equivalent or associated with a predisposition to a cancer.

The DNA can be obtained from canine p53 RNA by using a reverse transcriptase polymerase chain reaction (RT-PCR) and amplification.

A further step of the method may include, subsequent to obtaining and analysing the results, determining breed disposition to p53-dependent cancers whereby it is possible to select a healthy individual for a breeding programme or optionally de-select an individual with a germ line mutation from breeding.

Alternatively, the method of the invention may also comprise, following the step of obtaining a sample from the individual to be screened, isolating canine p53 RNA and comparing it to the canine p53 RNA sequence (SEQ ID NO:4) as set forth in FIG. 3 of the accompanying drawing, or a modified form thereof which is functionally equivalent or associated with a predisposition to a cancer.

In another embodiment of the method of the invention, following the step of obtaining a sample from the individual to be screened, the method comprises isolating the canine p53 protein and comparing it to the canine p53 protein sequence (SEQ ID NO:2) as set forth in FIG. 4 of the accompanying drawing, or a modified form thereof which is functionally equivalent or associated with a predisposition to a cancer.

Preferably the sample is obtained from blood or tissue of the individual to be screened.

DESCRIPTION OF THE DRAWINGS

The present invention will now be described, by way of example only, and with reference to the accompanying drawings, in which:

FIG. 1 shows the sequence (SEQ ID NO:5; SEQ ID NO:6) of the degenerate oligonucleotides used in the isolation of canine p53 cDNA;

FIG. 2 shows the complete cDNA sequence (SEQ ID NO:1) of canine p53;

FIG. 3 shows the canine p53 RNA sequence (SEQ ID NO:4)

FIG. 4 shows the canine p53 protein sequence (SEQ ID NO:2)

FIG. 6 shows clinical information of canine lymphoma patients analysed for p53 gene status;

FIG. 8 shows clinical information on canine mammary cancer patients;

DESCRIPTION OF SPECIFIC EMBODIMENTS

Materials and Methods

Plasmids and Bacterial Strains

Figure 5:
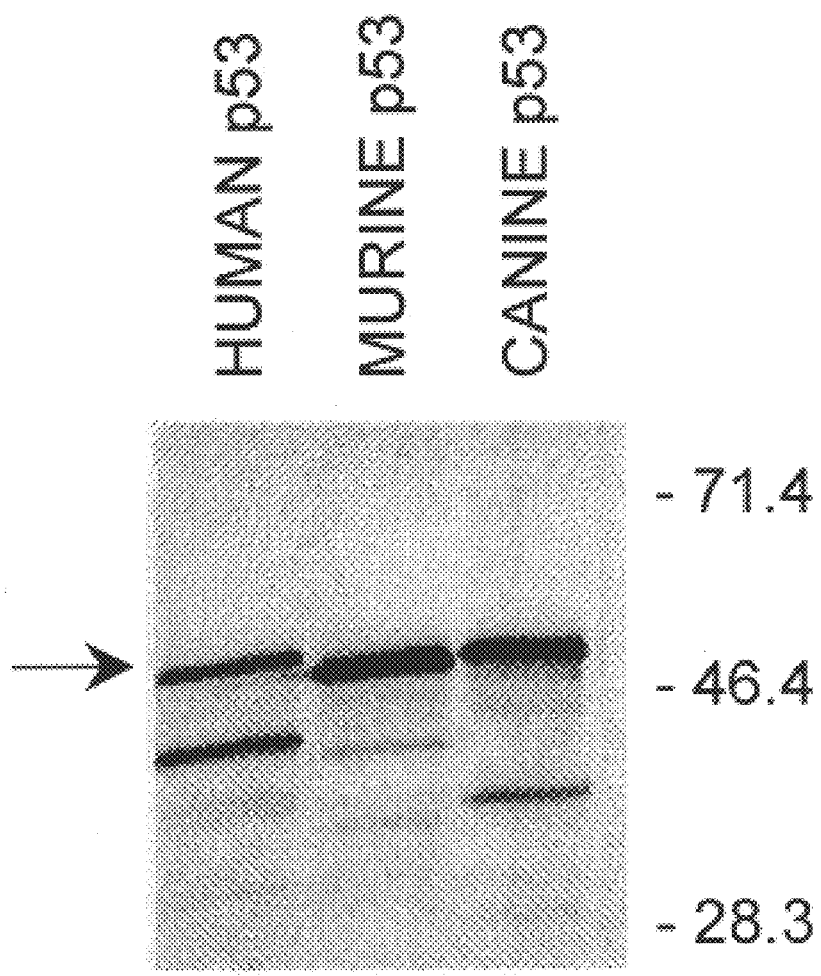
FIG. 5 shows the migration of in vitro translated p53 protein on a polyacrylamide gel.

The canine p53 cDNA was cloned into pLitmus 29 and called pK9. The canine p53 mutant cDNA construct cp53ΔN was cloned into pcDNA3 to create the expression plasmid pc3CΔN. Plasmids pc3C contained the canine p53 cDNAs, cloned into the mammalian expression plasmid pcDNA3. Plasmids were maintained in *E. coli* XL-1 Blue MRF'.

RNA Isolation and RT-PCR Amplification

Total RNA was prepared from $10^7$ peripheral blood leukocytes (PBL) isolated from a healthy one year old collie-retriever cross using the RNeasy RNA isolation kit as per the manufacturer's protocol (Qiagen). Complementary DNA fragments containing p53 coding sequence were amplified from 2 μg total RNA using the Access RT-PCR system as per the manufacturers protocol (Promega). A 5' p53 cDNA fragment was prepared using the primers 5'up and cp53dn while a 3' p53 cDNA fragment was isolated using the primers cp53up and 3'dn. The 5' and 3' cDNA fragments were cloned into pTZRJL1 and pLitmus 29, respectively, and DNA sequencing was performed. From the sequence information obtained, the primers NTup and CTdn were generated and used in RT-PCR amplification of the complete canine p53 cDNA from canine PBL which was cloned into pLitmus 29 and called pK9.

Construction of Canine p53 Mutant cp53ΔN

Mutant canine p53 protein containing a deletion of the N-terminal domain was constructed by cDNA amplification and cloning. The 100 μl amplification reaction contained 10 mM Tris-HCl (pH 8.75 at 20° C.), 25 m M KCl1,5 mM $(NH_4)_2SO_4$, 2 MM $MgSO_4$, 200 μM dNTPs (dATP, dCTP, dGTP, dTTP), 0.25 μM each of primers ΔNup and CTdn, 1ng pK9, and 2.5 units Pwo polymerase (Boehringer). The thermocycle program included a denaturation step at 94° C. (7min), 30 cycles of 94° C. (30s), 55° C. (30s), 72° C. and a final elongation step at 72° C. (7 min). The amplified DNA product was digested with Kpn I and Bam HI and cloned into pcDNA3 to create pc3CΔN.

Transcription and Translation

Plasmid pK9 containing the canine p53 cDNA was digested with Eco RI. Each 50 μl transcription reaction contained 40 mM Tris-HCI pH 7.5, 6 mM $MgCl_2$, 2 mM spermidine, 10 mM dithiothreitol, 20 units RNasin (Promega), 0.5 mM each ATP, CTP and UTP, 0.025 mM GTP, 2 µg template DNA, 0.5 mM $m^7GpppG$, and 40 units T7 RNA polymerase (Promega). Transcription was allowed to proceed at 37° C. for 30 minutes and GTP was added to a final concentration of 1 mM. A further incubation of 60 minutes at 37° C. was performed followed by phenol:chloroform exaction, ethanol precipitation, and resuspension in 40 µl of water. The yield and purity of mRNA was estimated by agarose gel electrophoresis.

Canine p53 protein was were translated in a rabbit reticulocyte lysate system as described previously by Gamble and Milner (1988). A typical translation mix contained 70% (v/v) rabbit reticulocyte lysate (Promega), 2% (v/v) amino acid mix without methionine (Promega), and 10% (v/v) [$^{35}$S]-methionine (40.5 TBq/mmol; Amersham). The translation mix and template mRNA were preincubated for 10 minutes at 30° C. and 67° C., respectively. Template mRNA was then added to the translation mix at a final concentration of 8% (v/v) and the reaction allowed to proceed for 90 minutes at 30° C. and then stored on ice. The efficiency of translation was determined by TCA precipitation on glass filters followed by scintillation counting. Protein was resolved on a 15% polyacrylamide gel and visualised by antoradiography with Fuji RX film at room temperature.

Immunoprecipitation

Protein conformation was determined by immunoprecipitation with anti-p53 antibodies as described by Cook and Milner (1990). The following antibodies were used: DO1, Pab1801, Pab242, Pab248, Pab246, Pab1620, Pab240 and Pab421. Antibody Pab416, directed towards the large T-antigen of SV40, was used as a negative control. Immunoprecipitated proteins were resolved by 15% SDS-polyacrylamide gel electrophoresis and visualised by autoradiography with Fuji RX film at room temperature.

DNA binding and Proteolytic Cleavage

Analysis of p53 DNA binding activity and proteolytic cleavage was performed as described previously by Molinari et al (1996) and Okovokov et al (1997). Binding to specific DNA sites was assessed using the biotinylated double stranded oligonucleotides CON (Funk et al 1992), p21 (oligonucleotides p21up/p21dn), and GADD45 (oligonucleotides GADD45up/GADD45dn). Binding activity to damaged DNA targets was determined by using biotinylated lesion (L-DNA; oligonucleotides Lup and L/NLdn) and non lesion (NL-DNA; oligonucleotides NLup and L/NLdn) double stranded DNA (Lee et at 1995) and single strand DNA (ssDNA; oligonucleotide L/NLdn). Streptavidin-magnetic beads (15 µl) coated wit 30 pmol target DNA oligonucletides were prepared as described by the manufacturer (Dynal) and then washed twice with 300 µl DNA binding buffer containing 20 mM Tris-HCI (pH 7.5 at 20° C.), 100 NaCl, 0.1% NP40, 6% glycerol and 5 mM DTT. The beads were subsequently incubated in 100 µl DNA binding buffer containing 20 µl translated p53 protein for 20 minutes at 20° C. The protein-DNA complexes were washed three times with 400 µl DNA binding buffer and resuspended in 30 µl Laemmli's buffer (Laemmli, 1970).

The DNA binding reaction prepared for the analysis of p53 proteolytic cleavage was identical to that described above. However, following the three washes of protein-DNA complexes with 400 µl DNA binding buffer the supernatant was removed and the beads resuspended in 50 µl DNA binding buffer and incubated at 37° C. for one hour. Protein-DNA complexes retained on the beads were collected and the supernatant saved for analysis. The beads were washed three times with 400 µl DNA binding buffer mad resuspended in 30 µl Laemmli's buffer. Protein retained on the DNA and released into the supernatant were analysed by 15% SDS-PAGE.

Transfection Assays

The primary murine p53 null fibroblast cell line (1° MEFs) was prepared as described by Harvey et at (1993). Cells were cultured at 37° C. in an atmosphere of 5% $CO_2$ in air in Dulbecco's modified Eagle's (DMEM) media (Gibco) supplemented with 10% foetal calf serum, 2 mM L-glutamine and 100 U/ml penicillin/streptomycin (Gibco). For maintenance the cells were cultured in 25 $cm^3$ and 75 $cm^3$ flasks and passaged 1 in 8 at approximately 70% confluency.

Plasmids for transfection were prepared using a midi-prep kit as described by the manufacturer (Qiagen). The reporter plasmid, pRGCΔfosLacZ, contains the LacZ gene under the control of a p53-inducible promoter (Frebourg et al 1992). The expression vector pc3C contains the canine p53 cDNA under the control of the cytomegalovirus (CMV) promoter. Cells were seeded onto 8 cm dishes at 30% confluency, 18 hours before transfection. Cotransfections were carried out with Lipofectamine and Opti-MEM as per the manufacturers protocol (Gibco). Ten micrograms of p53 expression plasmid, 10 µg of reporter plasmid, and 50 µl lipofectamine were used per 8 cm dish. The level of β-galactosidase expression was determined 48 hours post-transfection using an ONPG assay as described by Rosenthal (1987).

Clinical Features of Canine Patients with Lymphomas

The clinical information for eight can patients are shown in FIG. 6. The primary lymphomas of patients 4 and 5 were classified as T-cell in origin based on the presence of TCR β chain rearrangements. The primary tumours of the remaining six patients were classified as B-cell lymphomas. The level of P-glycoprotein expression was determined in normal livers and tumour tissue samples from each canine patient by immunohistochemical staining. A minimum of two independent tissue samples were stained and those with over 80% P-glycoprotein positive cells were scored as positive (FIG. 6). Only two out of the eight lymphomas were positive for P-glycoprotein expression (patients 7 and 8) and interestingly, neither responded to treatment. Patient 8 showed a therapy-related increase in P-glycoprotein expression, whereas patient 7 displayed increased levels of P-glycoprotein before and after chemotherapy.

Clinical Features of Canine Patients with Mammary Tumours

The P53 status was determined in 10 canine patients. The p53 cDNA was isolated from normal and tumour tissue using reverse transcription and DNA amplification. DNA sequencing identified p53 mutations in three out of the ten patients.

Results

Evidence for Sequence Data

As indicated above, the isolation of canine p53 cDNA was carried out using a reverse transcriptase polymerase chain reaction (RT-PCR) method and a combination of degenerate and canine p53-specific primers. Initially, cDNA encompassing the 5' and 3' halves of the canine p53 open reading frame were amplified from total RNA isolated from the peripheral blood leukocytes of a healthy dog. Primer pairs 5'up/cp53dn and cp53up/3'dn (FIG. 1; SEQ ID NO:5; SEQ ID NO:6) were used in the RT-PCR and the amplified cDNAs were cloned and sequenced. The canine p53 cDNA sequence (SEQ ID NO:1) information obtained was then used to design a second primer pair (NTup and CTdn) specific for the initiation and termination sites of the canine p53 open reading frame. RT-PCR amplification using these primers resulted in the isolation of a 1174 base pair cDNA product (SEQ ID NO:1) (FIG. 2) encoding the complete 1146 base pair open reading frame of canine p53 (FIG. 3) (SEQ ID NO:1). The cDNA sequence encoding amino acids 25 to 300 is identical to that previously reported (Kraegel et al 1995).

Canine p53 protein was expressed in vitro in rabbit reticulocyte lysate and labelled with $^{35}$S-methionine (Gamble and Milner, 1988; Cook and Milner, 1990). The protein co-migrates with human p53 protein and displays an apparent molecular mass of between 48 and 55kDa (FIG. 5).

Evidence for Germ-Line p53 Mutations

Figure 7:
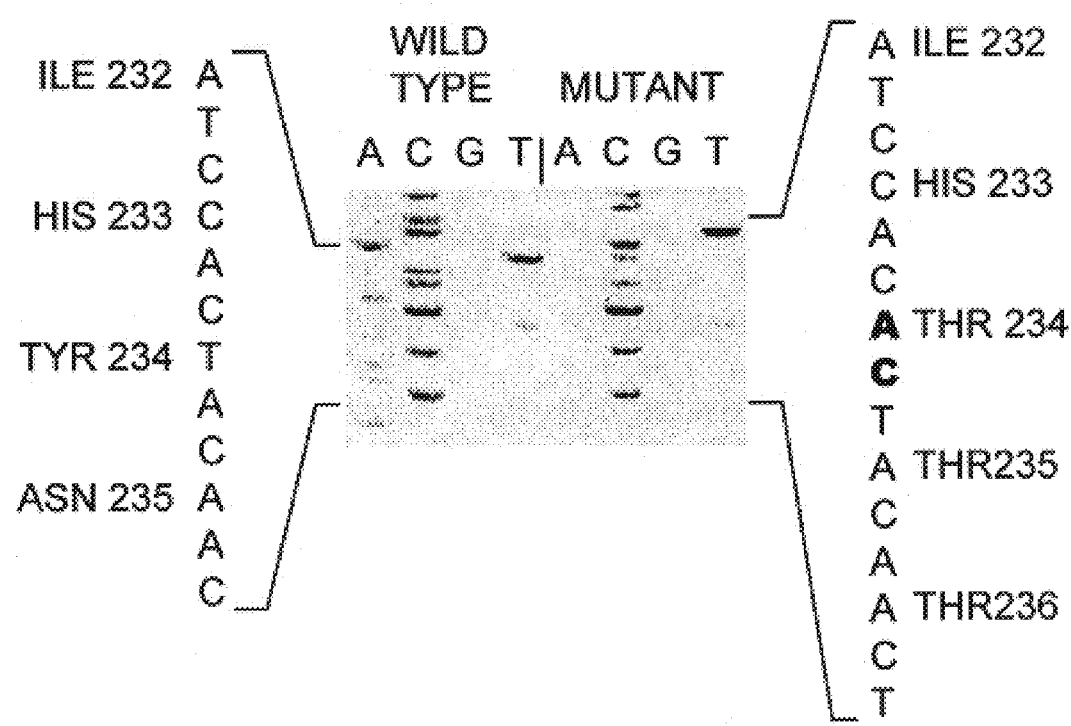
FIG. 7 shows in patient 1 of FIG. 6.

Patient 1 identified from FIG. 6 proved to be heterozygous for p53 in both normal and tumour samples (FIG. 7). Both wild and mutant type alleles isolated from the secondary lymphoma are shown in FIG. 6 (SEQ ID NO:7; SEQ ID NO:8) and a two base pair insertion at codon 234 in exon 7 of the mutant allele is denoted in bold face. This finding was confirmed in both liver and peripheral blood samples. The presence of a p53 mutant in normal tissue indicates that the mutation was inherited through the germ line.

With reference to the canine patients diagnosed as suffering from mammary tumours (FIG. 8), two patients were found to have tumour associated p53 mutations within exons 2 and 5, while a third contained germ line deletion of exons 3 to 7 of the p53 gene.

Figure 9:
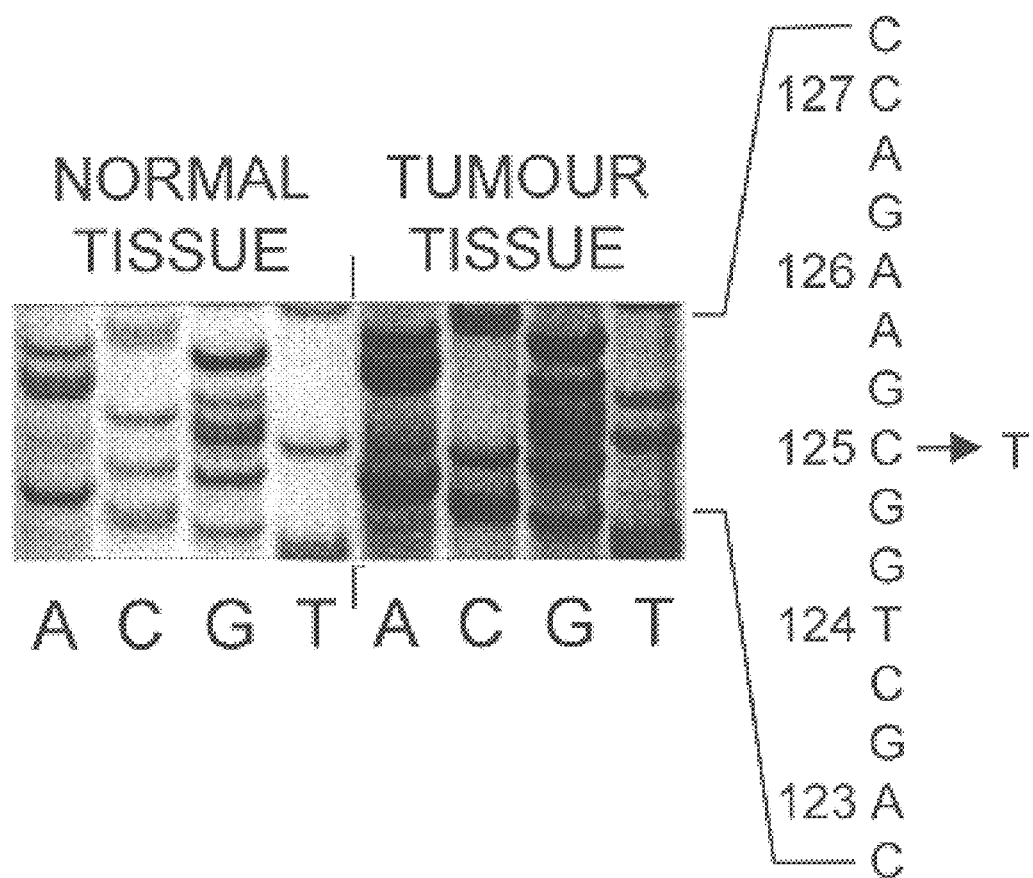
FIG. 9 shows sequence identification (SEQ ID NO:9) of a mutant p53 allele within a solid mammary carcinoma from patient 5 of FIG. 8.

FIG. 9 represents the identification of a mutant allele within the solid mammary tumour from patient 5. The exon 5 p53 cDNA sequence from normal and tumour tissue is shown(SEQ ID NO:9) along with the non-coding strand sequence substitution. Codon positions are shown to the left of the DNA sequence.

Figure 10:
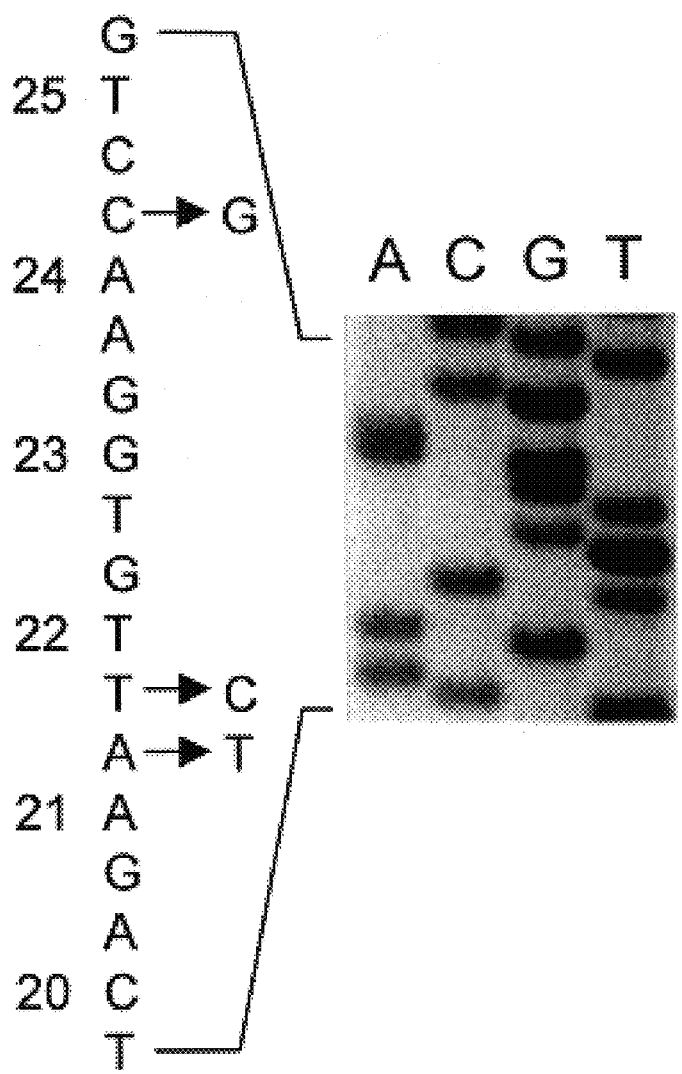
FIG. 10 shows the tumour-associated mutant p53 allele sequence (SEQ ID NO:10) with patient 6 of FIG. 8.

FIG. 10 represents the identification of a tumour associated mutant p53 allele within patient 6. The exon 2 p53 cDNA sequence from mammary tumour tissue is depicted (SEQ ID NO:10) along with the non-coding strand sequence substitutions. Codon positions are shown to the left of the DNA sequence.

Figure 11B:
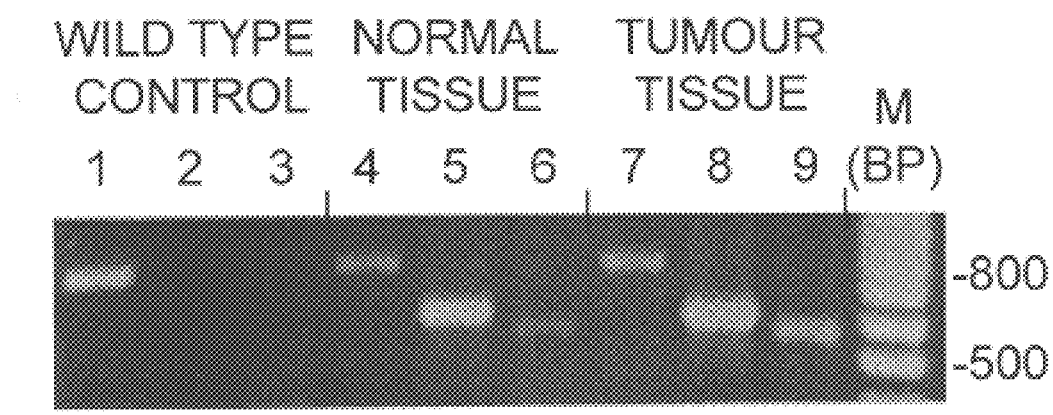
FIG. 11 shows the sequence characterisation (SEQ ID NO:3) of a germ line deletion within one p53 allele of patient 9 of FIG. 8.
Figure 12:
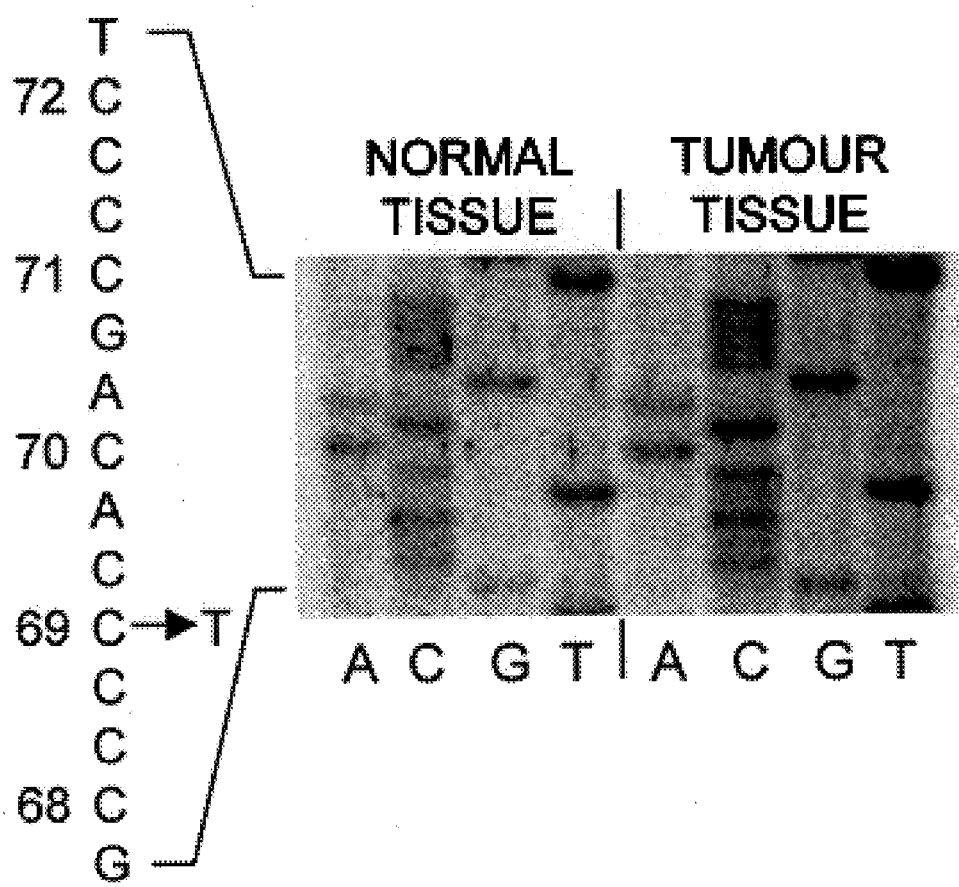
FIG. 12 shows the location of a single base pair substitution within intact p53 allele sequence ((SEQ ID NO:11) of patient 9 of FIG. 8.

FIG. 11 shows the characterisation of a germ line deletion within one p53 allele of patient 9. FIG. 11 shows the DNA sequence (SEQ ID NO:3) of the p53 allele from patient 9 containing a deletion of exons 3 to 7. Exons are boxed. The dashed vertical line shows the proposed location of the DNA deletion event. In FIG. 11B shows the direct detection of p53 deletion mutation within genomic DNA isolated from normal (lanes 5 and 6) and tumour (lanes 8 and 9) tissue. Amplification of exons 5 to 7 from the second intact p53 allele isolated from normal and tumour tissue is also shown (lanes 4 and 7). Genomic DNA isolated from a healthy dog were included as a wild type control (lanes 1 and 3). Further investigations with patient 9 are shown in FIG. 12. FIG. 10 shows the location of a single base pair substitution (SEQ ID NO:11) within the intact p53 allele. DNA sequence from exon 4 of the p53 gene isolated from normal and tumor tissue is shown. The C to T transition at codon 69 is depicted, codon positions are shown to the left of the non-coding strand DNA sequence.

Figure 13:
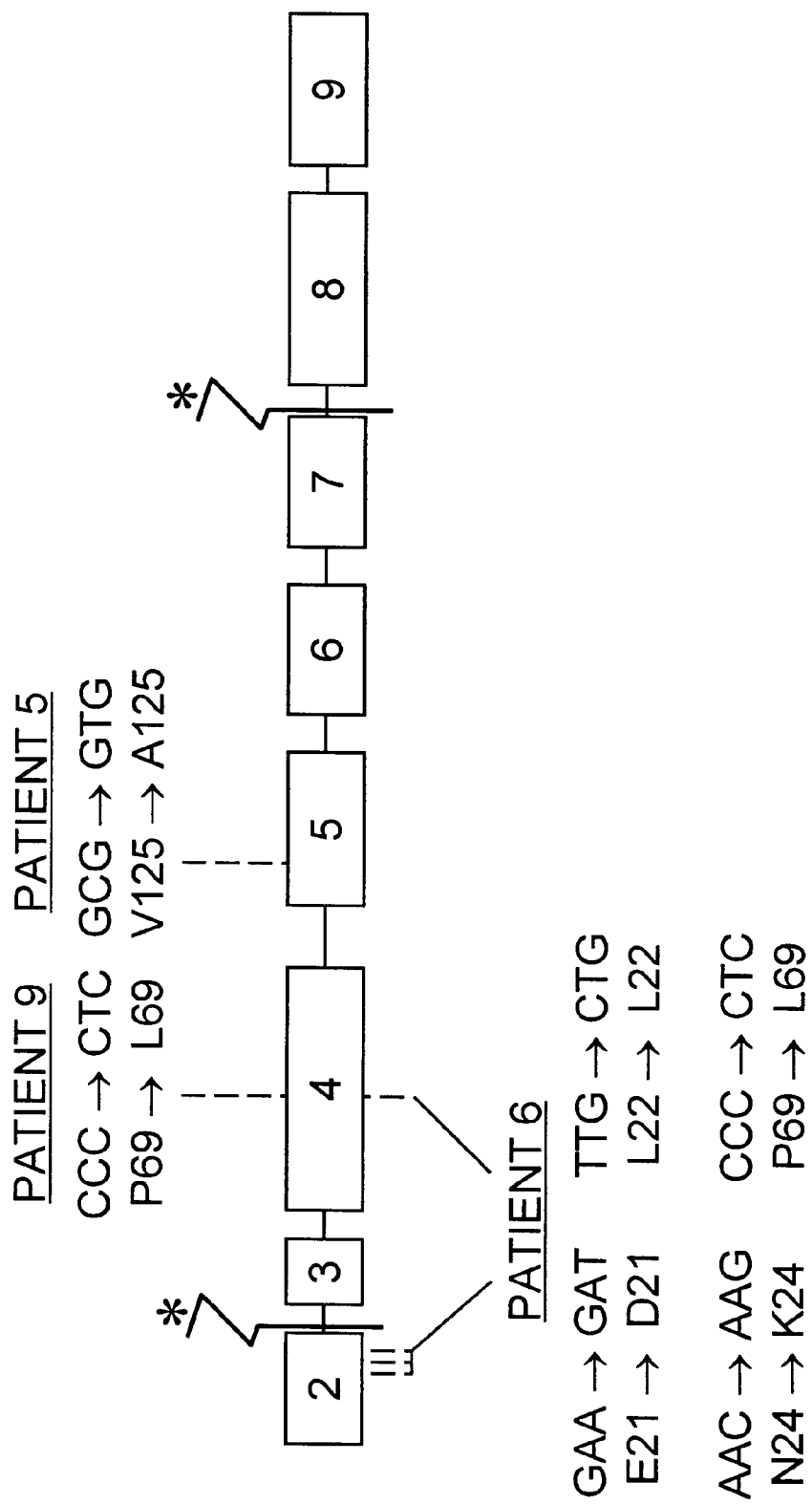
FIG. 13 represents a summary of DNA sequence changes identified in the p53 gene of patients 5, 6 and 9 of FIG. 8.

The evidence for germ line mutations from canine patients suffering from mammary tumours can be summarised in FIG. 13. The position of each point mutation in the DNA sequence identified in the three patients (5, 6 and 9) is represented by dashed lines. The location of DNA breaks within one p53 allele of patient 9 is shown by an asterisk.

Thus, from the foregoing evidence the present invention therefore provides a method for identifying p53 gene mutations and so can be invaluable in the outbreeding of an inherited predisposition to cancer in the dog.

What is claimed is:

1. An isolated DNA coding for the canine p53 protein encoded by the DNA sequence given as SEQ ID NO:1.

2. An isolated DNA sequence according to claim 1 having the DNA sequence given as SEQ ID NO:1.

3. A replicative cloning vector comprising an isolated DNA according to claim 1 and a replicon operative in a host cell for said vector.

4. A host cell containing a vector according to claim 3.

5. An expression vector comprising an isolated DNA according to claim 1 operably linked to a promoter sequence that directs expression of said isolated DNA in host cells for said vector.

6. A host cell containing a vector according to claim 5.

7. A method of producing a canine p53 protein comprising culturing host cells according to claim 6 under conditions suitable for production of the protein encoded by said isolated DNA, and then recovering said protein.

* * * * *